United States Patent [19]

Besenyei et al.

[11] Patent Number: 5,068,424

[45] Date of Patent: Nov. 26, 1991

[54] PROCESS FOR PREPARING ARYLSULPHONYL-ISOCYANATES AND ADDITION DERIVATIVES THEREOF

[75] Inventors: Gábor Besenyei; Sándor Németh; László Simándi; Mária Belák, all of Budapest; József Dukai, Veszprém; Lajos Nagy, Füfögyártelep; Elemér Tömördi, Veszprém; Csaba Söptei, Veszprém; Erzsébet E. Diószeginé, Veszprém, all of Hungary

[73] Assignees: Nitrokémia Ipartelepek; Magyar Tudományos Akadémia Központi Kémiai Kutató Intézete, both of Budapest, Hungary

[21] Appl. No.: 365,790

[22] Filed: Jun. 14, 1989

[30] Foreign Application Priority Data

Jun. 17, 1988 [HU] Hungary .................. 3115/88
Jul. 22, 1988 [HU] Hungary .................. 3887/88
Jul. 22, 1988 [HU] Hungary .................. 3888/88

[51] Int. Cl.⁵ .......................................... C07C 263/00
[52] U.S. Cl. .................................. 562/870; 558/61
[58] Field of Search ..................... 558/61; 562/870

[56] References Cited

U.S. PATENT DOCUMENTS 3,371,114  2/1968  Sayigh et al. .................. 562/870
4,379,769  4/1983  Levitt ............................ 562/870

Primary Examiner—Jose G. Dees
Assistant Examiner—Vera C. Clarke
Attorney, Agent, or Firm—Schweitzer Cornman & Gross

[57] ABSTRACT

The invention relates to a process for preparing arylsulphonyl isocyanates of the general formula (I)

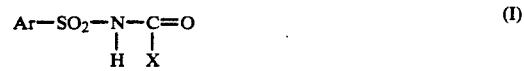

and addition derivatives thereof—where in the formula the meaning of the substituents are as follows:

Ar represents optionally substituted aryl, naphthyl- or thienyl group, and
HX is a chemical bond or X
$ZR_1$ stands for a group where Z is oxygen or sulphur, $R_1$ is saturated or unsaturated alkyl, benzyl, cyclohexyl or substituted phenyl group or
X is an $NR_2R_3$ group wherein $R_2R_3$ is hydrogen, alkyl, unsubstituted alkyl, aryl, substituted aryl, aroyl or acyl group, and the essence of the process is that an N-halogen sulphonamidate is carbonylated in the presence of a carbonylating catalyst, in the presence or absence of alcohol, (thio) alcohol or amine reactants and the carbonylated compound obtained is reacted subsequently with the reactants.

8 Claims, No Drawings

PROCESS FOR PREPARING ARYLSULPHONYL-ISOCYANATES AND ADDITION DERIVATIVES THEREOF

The invention relates to a new process for preparing arylsulphonyl isocyanates and the addition derivatives thereof, such as arylsulphonyl carbamates and thiocarbamates as well as arylsulphonylureas of general formula (I).

$$\text{Ar}-SO_2-\underset{H}{N}-\underset{X}{C}=O \qquad (I)$$

Several utilizable compounds having biological activity can be found among arylsulphonyl carbamic acid derivatives. In case of O-esters and S-esters the moderation of the phytotoxic effect of triazine and this carbamate-type herbicides were observed, while N-(arylsulphonyl)-N'-alkylureas are known first of all for their activity decreasing the blood-sugar level. In addition the arylsulphonyl isocyanates and carbamates are starting materials for modern medicines and plant-protecting agents.

The methods for preparing arylsulphonyl isocyanates are summarised as follows:

Arylsulphonyl isocyanates are most frequently prepared by the reaction of arylsulphonamides and phosgene (GB 692,360/CA 47 8771e/)

$$ArSO_2NH_2 + COCl_2 \rightarrow ArSO_2NCO + 2HCl \qquad (1)$$

The presence of catalytic amounts of aliphatic isocyanates (J. Org. Chem. 1966, 31, 2658) or aliphatic amines (DE 2,152,971) makes it considerably easier to carry out the phosgenation reaction.

By reacting aromatic sulphonamides with oxalyl chloride also arylsulphonyl isocyanates are obtained (J. Org. Chem. 1964, 29, 2592):

$$ArSO_2NH_2 + (COCl)_2 \rightarrow ArSO_2NCO + 2HCl + CO \qquad (2)$$

Arylsulphonyl isocyanates can also be prepared by treating arylsulphonamides first with thionyl chlorides, then the intermediate N-sulphinyl-sulphonamides are reacted with phosgene (J. Org. Chem., 1969, 34, 3200)

$$ArSO_2NH_2 \xrightarrow[-2HCl]{SOCl_2} ArSO_2NSO \xrightarrow{COCl_2} ArSO_2NCO \qquad (3)$$

The double exchange of arylsulphonyl chlorides and trimethylsilyl isocyanate in the presence of titanium tetrachloride also affords arylsulphonyl isocyanates (DE 3,235,045):

$$ArSO_2Cl + Me_3SiNCO \xrightarrow{TiCl_4} ArSO_2NCO \qquad (4)$$

As an easy possibility for preparing arylsulphonyl carbamates and thiocarbamates, the reaction of arylsulphonyl isocyanates with alcohols and mercaptanes can be mentioned (J. Heterocycl. Chem., 1980, 17, 271 and its references):

$$ArSO_2NCO + RZH \rightarrow ArSO_2NHC(O)ZR \qquad (5)$$

$$Z = O, S$$

Arylsulphonyl carbamic acid esters and thioesters can also be prepared by reacting arylsulphonamides with chloroformic acid esters or chlorothioformic acid esters (J. Org. Chem., 1958, 23, 923, DE 2 644 446):

$$ArSO_2NH_2 + ClC(O)ZR \xrightarrow{-HCl} ArSO_2NHC(O)ZR \qquad (6)$$

Arylsulphonyl carbamates are also obtained by using carbonic acid esters as acylating agent (U.S. Pat. No. 4,612,385, EP 96,003):

$$ArSO_2NH_2 + (RO)_2CO \xrightarrow[\text{NaH, solvent}]{-ROH} ArSO_2NHC(O)OR \qquad (7)$$

The addition reaction of primary or secondary amines with sulphonyl isocyanates are widely used for preparing arylsulphonylureas (Chem. Rev. 1965, 65, 369-76 and its references):

$$ArSO_2NCO + HNR_1R_2 \rightarrow ArSO_2NHC(O)NR_1R_2 \qquad (8)$$

The reaction of sulphonamides with aliphatic isocyanates results also 1,3-substituted ureas (Ger. 1,201,337):

$$ArSO_2NH_2 + RNCO \rightarrow ArSO_2NHC(O)NHR \qquad (9)$$

The reaction or arylsulphonyl carbamates with primary or secondary amines (J. Org. Chem., 1958, 23, 923-9) or the interaction of arylsulphonamides with N-substituted carbamic acid esters (Brit 604.259 (CA 43 1061b/1949/)) also affords arylsulphonylureas:

$$ArSO_2NHC(O)OR + HNR_1R_2 \xrightarrow{-ROH} ArSO_2NHC(O)NR_1R_2 \qquad (10)$$

$$ArSO_2NH_2 + R_1R_2NC(O)OR \xrightarrow{-ROH} ArSO_2NHC(O)NR_1R_2 \qquad (11)$$

The reaction of carbamoyl chlorides and sulphonamides affords in sulphonylureas with liberation of hydrochloric acid (GB PS 538,884/CA 36 3511/1942//). Carbamoyl chlorides are generally prepared by reacting primary or secondary amines with phosgene and the product is used mostly without isolation.

$$ArSO_2NH_2 + R_1R_2NC(O)Cl \xrightarrow{-HCl} ArSO_2NHC(O)NR_1R_2 \qquad (12)$$

Most of the known processes are based on the direct or indirect use of phosgene. The preparation, delivery, storage and use of phosgene is always a potential source of danger, therefore, efforts are constantly being made for their elimination. In addition to problems of environmental protection caused by its toxicity, hydrochloric acid formed during the phosgenation reaction causes corrosion damage, and requires the use of special construction materials for technological equipment. In spite of the high reactivity of phosgene, arylsulphonyl isocyanates can only be prepared at relatively high temperatures In cases (Me$_3$SiNCO, NaH) very sensitive to water should also be used. In order to eliminate all these problems of environmental pollution, energy use and technology, new process for preparing arylsulphonylcarbamic acid derivatives seemed to be necessary. In our continuing search for synthetic methods for preparing N-(arylsulphonyl)-urea acid derivatives, it was found that the target compounds of the general formula (I) can also be obtained by reacting an N-halosulphonamidate of general formula (II)

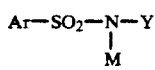 (II)

with CO in the presence of a carbonylating catalyst, or carbonylating an N-haloarylsulphonamidate of general formula (II) in the presence of an alcohol of general formula (III)

 (III)

or an amine of general formula (IV)

 (IV)

or reacting the N-halosulphonamidate of general formula (II) with carbon monoxide in the presence of a catalyst, then treating the reaction mixture obtained with reactants of general formula (III) or (IV).

The process according to the invention for preparing arylsulphonyl isocyanates of general formula (I) and addition derivatives thereof—wherein Ar represents a phenyl, naphthyl or thienyl group, the derivatives thereof substituted by $C_{1-4}$ alkyl, $C_{1-4}$ haloalkyl, (halo)alkyloxy, nitro, cyano groups or halogen atoms, HX represent together a chemical bond or X stands for $ZR_1$ group—wherein Z is an oxygen or sulphur atom, $R_1$ stands for $C_{1-8}$ alkyl, allyl, propargyl, $C_{1-4}$ haloalkyl, cyclohexyl, benzyl or (substituted) phenyl group, or X stands for an $NR_2R_3$ group—wherein $R_2$ and $R_3$ independently from each other represent hydrogen atom, $C_{1-6}$ alkyl, allyl, cyclohexyl, alkoxycarbonyl, aryloxycarbonyl, arylsulphonyl, $C_{2-4}$ acyl, (substituted) benzoyl group, or $R_2$ and $R_3$ together an α, ω-alkylene group having 4-6 carbon atoms which may include an oxygen atom, but $R_2$ and $R_3$ simultaneously cannot be hydrogen atoms, can be characterized by, a) carbonylating an N-haloarylsulphonamidate of general formula (II)—wherein Ar is as defined above, Y stands for a chlorine or bromine atom, M represents sodium ion, potassium ion, quaternary ammonium ion, quaternary phosphonium ion— in the presence of a carbonylating catalyst, carbon monoxide and optionally a phase transfer catalyst (reaction scheme A) or b) reacting an N-haloarylsulphonamidate of the general formula (II) in the presence of a carbonylating catalyst, carbon monoxide, an alcohol of the general formula (III)—wherein Z stands for oxygen atom, $R_1$ is as defined above— and optionally in the presence of a phase transfer catalyst (reaction scheme B)

c) reacting the N-haloarylsulphonamidate of the general formula (II) in the presence of a carbonylating catalyst, carbon monoxide, amine of the general formula (IV)—wherein $R_2$ and $R_3$ are as defined above— and optionally in the presence of a phase transfer catalyst (reaction scheme C) or d) reacting the reaction mixture obtained according to synthetic scheme A) with alcohols or thioalcohols of general formula III or with amines of general formula IV, wherein Z, $R_1$, $R_2$ and $R_3$ are as defined above.

Reaction scheme A)

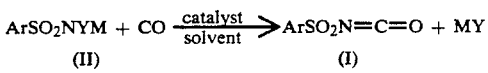

Reaction scheme B)

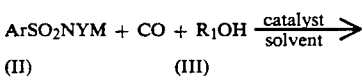

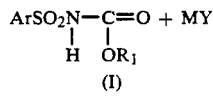

Reaction scheme C)

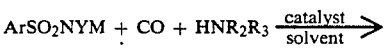

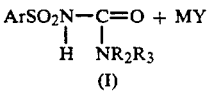

As carbonylating catalyst, a palladium containing complex synthesised previously or prepared in situ in the reaction mixture is used, where the coordinative bond is formed by carbon, nitrogen, oxygen, phosphorus, sulphur and/or halogen atoms, in the form of homogeneous, heterogeneous or immobilised homogeneous catalyst, in an amount of $10^{-2}-10$ weight % with respect the mass of the starting N-halogen compounds.

Phase transfer catalyst can also be used in an amount of $10^{-1}-10$ weight % referred to the mass of the starting N-halogen compound. The reaction medium is an organic solvent, temperature is between $-20°$ and $130°$ C., the starting partial CO pressure is 0.3-10 MPa, the reaction time is 0.5-24 hours. The reaction mixture is processes in a known manner.

A preferred starting compound is a sulphonamidate of the general formula (II), wherein Y is chlorine atom, M is potassium ion.

As preferred starting compound a sulphonamidate of the general formula (II) can also be mentioned, wherein Y represents chlorine atom, and M is a quaternary ammonium ion.

The palladium catalyst can be used together with carbonyls of metals belonging to group VI of the periodic system and/or with complexes of metals belonging to group VIII of the periodic system.

An essential difference from the known processes described by equations (1)-(12) is that arylsulphonyl arylsulphonyl isocyanates and arylsulphonyl carbamic acid derivatives are prepared without using phosgene; and certain the end product can be prepared from the starting compounds in a single step.

Important advantages of the process according to the invention can be summarized as follows:

use of phosgene is not necessary, so the process is less hazardous and does not endanger the environment as do the known ones;

N-halogen compounds used as starting compounds can be prepared with good yield from suitable starting materials by using inexpensive reagents (such as NaOCl, KOCl, Ca(OCl)Cl, $Cl_2$, $Br_2$, etc.);

both the carbonylating and the coupling reaction can be carried out at room temperature, so energy can be saved.

N-halosulphonamidates used as starting materials are known compounds in the art, their preparation methods are described in several literature references (see Methoden der Organischen Chjemie/Houben-Weyl/, Band IX, page 642, 1955; M. C. Campbell and G. Johnson: Chem. Rev., 1978 78/1/, 65-79. Bull. Chem. Soc. Jpn. 1984 57, 3341-2).

N-haloarylsulphonamidate can be used in previously prepared form or can be prepared alone in the reaction mixture by a suitable method and is further reacted without isolation.

According to the process of the invention, the synthesis of arylsulphonyl isocyanates and arylsulphonyl carbamic acid derivatives is carried out in a solvent. As reaction medium, most solvents generally used in organic chemistry can be used. The reaction is optionally carried out in chlorinated hydrocarbons having 1-2 carbon atoms, in benzene, toluene, in mono- or dichlorinated derivatives thereof, in lower aliphatic or simple aromatic acid nitriles (acetonitrile, benzonitrile). When preparing carbamates, an excess of alcohol can be used as reaction medium.

The carbon monoxide required in the carbonylating reaction can be used in pure form, or as a gas mixture, for example with nitrogen. Some catalysts or reactants, however, can be sensitive for the carbon monoxide diluting component, the amount and type of the diluting components allowable in case of certain catalysts and reactants can be different. The partial CO pressure of the reactor can be chosen between $10^5$ Pa and $10^7$ Pa.

The N-halogen derivatives of sulphonamides are generally weakly soluble in organic solvents. In order to achieve a suitable reaction rate the use of a phase transfer catalyst may be necessary. For this purpose, quaternary ammonium salts, quaternary phosphonium salts or crown ether type compounds can be used.

As crown ether type compounds
dicyclohexyl-18-crown-6,
18-crown-6, (1,4,7,10,13,16-hexaoxycyclooctadecane and dibenzo-18-crown-6
can be mentioned.

According to a process variant of the invention, an N-haloarylsulphonamidate of general formula (II) is reacted in the presence of a carbonylating catalyst, carbon monoxide and optionally in the presence of a phase transfer catalyst with reactants of general formula (III) or (IV). According to another process variant an N-halosulphonamidate of general formula (II) is subjected to catalytic carbonylation and the intermediate thus prepared is further reacted with compounds of general formula (III) or (IV). In case of the preparation of arylsulphonyl isocyanates, the reaction mixture naturally should not contain reactants of general formula (III) and (IV).

The process according to the invention is described in detail in the following, non-limiting Examples as follows. When it is not separately described; the amount of the starting N-halosulphonamidates is 0.01 mole, the volume of the solvent is 10 $cm^3$. The analysis of the reaction mixtures is carried out by IR spectroscopy, HPLC method and mass spectrometry.

EXAMPLE 1

2.7 g. (10 mmole) of N,2-dichlorobenzene-sulphonamidate was carbonylated in the mixture of 10 $cm^3$ of dichloromethane and 1.8 $cm^3$ of acetonitrile in the presence of 45 mg. of $PdCl_2$ under a starting CO pressure of 5.5 MPa for 2 hours, at a temperature of 65° C. After the pressure had become constant the reactor was cooled and the reaction mixture was transferred to a glass vessel under $N_2$. An aliquot part of the reaction mixture was diluted 25-fold with dry dichloromethane and the liquid was subjected to IR spectroscopic analysis in a liquid cell. The intensive band appearing at 2250 $cm^{-1}$ indicates the presence of 2-Cl-phenylsulphonyl isocyanate. To the diluted reaction mixture, 30 $\mu l$ of ethylalcohol was added and the IR test was repeated. Simultaneously with the disappearance of the isocyanate band from the IR spectrum, characteristic bands of free ethanol (3620 $cm^{-1}$), as well as of ethyl-2-chlorophenylsulphonyl carbamate (3350 $cm^{-1}$, 1760 $cm^{-1}$) could be observed. Most of the isocyanate content of the reaction mixture was isolated as the 2-chloroaniline derivative/N-(2-chlorophenyl)-sulphonyl-N'-(2-chlorophenyl)-urea/. According to HPLC analysis, the yield of the isocyanate was 92%.

Arylsulphonyl isocyanates were further prepared by using a similar method. The reactants and the reaction parameters are summarized in Table 1.

TABLE 1

Preparation of ureas of the general formula (I)

| | Ar | M | catalyst | complex forming agent | additive | solvent | Tempr. [°C.] | $P_{CO}$ [MPa] | Time [hour] | Yield [%] |
|---|---|---|---|---|---|---|---|---|---|---|
| 2 | phenyl | potassium ion | $PdCl_2$ 145 mg | $CH_3CN$ 0.2 $cm^3$ | — | $CH_2Cl_2$ | 25 | 4.0 | 6 | 70.8 |
| 3 | 4-Me-phenyl | potassium ion | $Pd(PhCN)_2Cl_2$ 128 mg | — | — | $CH_3CN$ | 25 | 4.2 | 0.45 | 89 |
| 4 | 4-Me-phenyl | sodium ion | $PdCl_2$ 47 mg | $CH_3CN$ 0.5 $cm^3$ | — | $CH_2Cl_2$ | 25 | 4.1 | 6 | 78 |
| 5 | 2-Br-phenyl | potassium ion | $Pd(Ph_3P)_2Cl_2$ 198 mg | PhCN 2.0 $cm^3$ | — | $CH_2Cl_2$ | 60 | 3.5 | 0.25 | 80 |
| 6 | 4-Me-phenyl | $Bu_4N^+$ | $PdCl_2$ 27 mg | $CH_3CN$ 0.2 $cm^3$ | — | $CH_2Cl_2$ | 25 | 5.0 | 2.5 | 71 |
| 7 | 2-naphthyl | potassium ion | $PD(PhCN)_2Cl_2$ 120 mg | $CH_3CN$ 2 $cm^3$ | $Et_3(PhCH_2)N^+Cl^-$ 100 mg | $CH_2Cl_2$ | 25 | 4.4 | 3.5 | 82 |
| 8 | 2-thienyl | sodium ion | $Pd(Ph_3P)_2Cl_2$ 170 mg | $CH_3CN$ 2 $cm^3$ | dicyclohexyl-18-crown-6 32 mg | $CH_2Cl_2$ | 25 | 4.0 | 4.0 | 72 |

TABLE 1-continued

Preparation of ureas of the general formula (I)

| | Ar | M | catalyst | complex forming agent | additive | solvent | Tempr. [°C.] | $P_{CO}$ [MPa] | Time [hour] | Yield [%] |
|---|---|---|---|---|---|---|---|---|---|---|
| 9 | 3,5-dichlorophenyl | potassium ion | Pd(Ph$_3$P)$_2$Cl$_2$ 100 mg | CH$_3$CN 2 cm$^3$ | — | CH$_2$Cl$_2$ | 25 | 3.5 | 3.0 | 67 |
| 10 | 4-Me-phenyl | potassium ion | [Pd(CO)Cl]$_n$ 110 mg | CH$_3$CN 1.0 cm$^3$ | — | 1,2 trichloro ethane | 40 | 3.0 | 2.0 | 85 |
| 11 | 4-Me-phenyl | sodium ion | Pd$_2$dba$_3$* 168 mg | — | Et$_3$(PhCH$_2$)N$^+$Cl$^-$ 80 mg | CH$_2$Cl$_2$ | 50 | 5.0 | 1.5 | 75 |
| 12 | 4-Me-phenyl | potassium ion | PdCl$_2$ 27 mg | CH$_3$CN 0.5 cm$^3$ | — | o-dichlorobenzene | 25 | 9.0 | 3.8 | 68 |
| 13 | 4-Me-phenyl | potassium ion | PdCl$_2$ 104 mg | — | 18-crown-6- 50 mg | PhCN | 70 | 4.0 | 1.0 | 87 |
| 14 | 2-Br-phenyl | potassium ion | Ph(Ph$_3$P)$_3$Cl 30 mg Pd(Ph$_3$P)$_2$Cl$_2$ 73 mg | PhCN 0.5 cm$^3$ | — | CH$_2$Cl$_2$ | 65 | 3.2 | 2.0 | 74 |
| 15 | 4-Me-phenyl | potassium ion | PdCl$_2$ 48 mg | CH$_3$CN 0.5 cm$^3$ | — | CH$_2$Cl$_2$ | 105 | 4.1 | 0.3 | 81 |
| 16 | 4-Me-phenyl | potassium ion | Mo(CO)$_6$ 100 mg Pd(Ph$_3$P)$_2$Cl$_2$ 100 mg | — | — | | 55 | 3.5 | 0.75 | 83 |
| 17 | 2-Br-phenyl | potassium ion | Pt(Ph$_3$P)$_4$ 21.5 mg Pd(Ph$_3$P)$_2$Cl$_2$ 66 mg | PhCN 0.5 cm$^3$ | — | CH$_2$Cl$_2$ | 80 | 4.0 | 1.0 | 75 |

*dba—dibenzyliden-acetone

EXAMPLE 18

2.12 g (7.7 mmole) of N,2-dichlorobenzenesulphonamide-K-salt was reacted in 10 cm$^3$ of acetonitrile for 1 hour in the presence of 0.39 g (8.5 mmole) of ethanol and 61 mg of PdCl$_2$ at a temperature of 15° C. under a CO pressure of 4.2 MPa. After the gas phase had been blown off, the reaction mixture was transferred into a glass vessel and the volatile components were removed by pumping. After recrystallization of the a solid residue 1.46 g (69%) of N-(2-chlorophenylsulphonyl)-carbamid acid ethyl ester was obtained.

By using similar processes further carbamates were prepared. The amounts of the target compounds in the raw reaction mixtures were determined by HPLC method (Table 2).

N-(arylsulphonyl) carbamates and N-(arylsulphonyl) thiocarbamates of general formula (I) were prepared according to process variant c) as follows:

EXAMPLE 24

2.4 g of potassium N-chloro-p-toluenesulphonamidate was carbonylated in 10 cm$^3$ of acetonitrile for 60 minutes in the presence of 127 mg of Pd(PhCN)$_2$Cl$_2$ at room temperature under starting carbon monoxide pressure of 4.0 MPa. After the pressure had become constant the gas phase was blown off and 0.7 g of ethanol was added to the reaction mixture with external heating under N$_2$ atmosphere. The reaction mixture was evaporated, then analysed by IR-spectroscopy as well as by HPLC method. The yield of ethyl-N-p-toluenesulphonyl carbamate was 85%.

TABLE 2

Preparation of H-(arylsulphonyl)-carbamates of the general formula (I)

| | Ar | M | catalyst | complex forming agent | additive | solvent | $P_{CO}$ [MPa] | Tempr. [°C.] | Time [hour] | R$_1$OH | Yield of (I) [%] |
|---|---|---|---|---|---|---|---|---|---|---|---|
| 19 | 4-Me-phenyl | potassium ion | PD(PhCN)$_2$Cl$_2$ 120 mg | — | — | CH$_3$CN | 4.2 | 25 | 3 | MeOH | 80 |
| 20 | 2-naphthyl | potassium ion | Pd(CH$_3$CN)$_2$Cl$_2$ 70 mg | CH$_3$CN 2 cm$^3$ | — | CH$_2$Cl$_2$ | 4.0 | 20 | 1.5 | MeOH | 70 |
| 21 | 2-bromo-phenyl | potassium ion | PdCl$_2$ 110 mg | — | — | CH$_3$CN | 3.5 | 20 | 2 | EtOH | 70 |
| 22 | phenyl | potassium ion | PdCl$_2$ 87 mg | — | Bu$_4$P$^+$Cl$^-$ 70 mg | CH$_3$CN | 4.0 | 20 | 1 | i-PrOH | 57 |
| 23 | 2-Cl-phenyl | potassium ion | PdCl$_2$ 80 mg | — | — | PhCN | 4.0 | 20 | 2 | EtOH | 70 |

Further carbamates and thiocarbamates were prepared by using similar processes (Table 3).

TABLE 3

| | Ar | M | catalyst | complex forming agent | additive | solvent | $P_{CO}$ [MPa] | Tempr. [°C.] | Time [hour] | R$_1$ZH | Yield of (I) [%] |
|---|---|---|---|---|---|---|---|---|---|---|---|
| 25 | 2-Cl-phenyl | potassium ion | PdCl$_2$ 56 mg | — | — | CH$_3$CN | 4.2 | 0 20 | 1 1 | CH≡C— CH$_2$OH 0.61 g | 72 |
| 26 | 4-Me-phenyl | sodium ion | PdCl$_2$ | CH$_3$CN | (PhCH$_2$) | CH$_2$Cl$_2$ | 4.0 | 20 | 5 | CH$_3$CH$_2$ | 82 |

TABLE 3-continued

| | Ar | M | catalyst | complex forming agent | additive | solvent | $P_{CO}$ [MPa] | Tempr. [°C.] | Time [hour] | $R_1ZH$ | Yield of (I) [%] |
|---|---|---|---|---|---|---|---|---|---|---|---|
| | | | 76 mg | 0.2 cm³ | $PH_3P^+Cl^-$ 70 mg | | | | | OH 0.5 g | |
| 27 | phenyl | potassium ion | $PdCl_2$ 145 mg | $CH_3CN$ 0.2 cm³ | — | $CH_2Cl_2$ | 4.0 | 25 | 6 | PhOH 1.0 g | 70 |
| 28 | 2-naphthyl | potassium ion | $Pd(PhCN)_2Cl_2$ 120 mg | $CH_3CN$ 2 cm³ | $Et_3(PhCH_2)$ $N^+Cl^-$ 100 mg | $CH_2Cl_2$ | 4.4 | 25 | 3.5 | MeOH 0.35 g | 80 |
| 29 | 4-Me-phenyl | $Bu_4N^+$ | $PdCl_2$ 47 mg | $CH_3CN$ 0.2 cm³ | — | $CH_2Cl_2$ | 5.0 | 25 | 2.0 | $CH_2=CH-$ $CH_2OH$ 0.65 g | 67 |
| 30 | 4-Me-phenyl | potassium ion | $Pd(PhCN)_2Cl_2$ 128 mg | — | — | $CH_3CN$ | 4.2 | 25 | 1.2 | butyl-SH 0.9 g | 84 |
| 31 | 4-Me-phenyl | potassium ion | $PD(PhCN)_2Cl_2$ 110 mg | — | 18-crown-6 50 mg | $CH_3CN$ | 3.7 | 25 | 0.8 | n-hexyl-SH 1.2 g | 80 |

EXAMPLE 32

1.35 g (5 mmole) of potassium N,2-dichlorophenyl-sulphonamidate was carbonylated in 10 cm³ of acetonitrile at 20° C. in the presence of 0.05 g of $Pd(PhCN)_2Cl_2$ and 0.45 g (6 mmole) of urethane under CO pressure of 4.5 MPa for 6 hours. After taking up the calculated amount of carbon monoxide, the reaction mixture was stirred at room temperature for further 6–8 hours, then evaporated. The solid residue was analysed by liquid chromatography and IR spectroscopy without further processing. The yield of the N-(2-chlorophenyl-sulphonyl)-N'-(ethoxycarbonyl)-urea was 95%.

Further urea derivatives were similarly prepared (Table 4). The amount of sulphonamidate was 5 mmole in every case.

for 60 minutes in the presence of 0.050 g of $Pd(PhCN)_2Cl_2$ at a temperature of 20° C. under a CO pressure of 4.2 MPa. After the taking up of the calculated amount of carbon monoxide, the gas phase was blown off and the reaction mixture transferred into a glass vessel under $N_2$ atmosphere, then 0.90 g (5 mmole) of dicyclohexylamine dissolved in 3 cm³ of acetonitrile was added dropwise under intensive cooling (0°–5° C.). After stirring for 30 minutes the reaction mixture was evaporated and the product purified by recrystallization. The yield of N-tosyl-N',N'-dicyclohexylurea was 1.45 g (76%).

Further ureas of general formula (I) were prepared similarly (Table 5). In the Table the reaction time of the carbonylating reaction is shown. The time of the coupling reaction in case of strongly basic amines is 5–30

TABLE 4

Preparation of ureas of the general formula (I)

| | Ar | M | catalyst | complex forming agent | additive | solvent | $P_{CO}$ [MPa] | Tempr. [°C.] | Time [hour] | (IV) reactant | Yield [%] |
|---|---|---|---|---|---|---|---|---|---|---|---|
| 33 | phenyl | potassium ion | $PD(PhCN)_2Cl_2$ 47 mg | — | — | $CH_3CN$ | 3.5 | 25 | 12 | urethane 0.5 g | 90 |
| 34 | phenyl | potassium ion | $Pd(Ph_3P)_2Cl_2$ 80 mg | $CH_3CN$ 2 cm³ | — | $CH_2Cl_2$ | 3.7 | 40 | 8 | acetamide 0.3 g | 87 |
| 35 | 4-Me-phenyl | potassium ion | $PdCl_2$ 50 mg | — | 18-crown-6 50 mg | $CH_3CN$ | 4.0 | 25 | 18 | 4-MeO-benzamide 0.8 g | 78 |
| 36 | 4-Me-phenyl | $Bu_4N^+$ | $PdCl_2$ 40 mg | — | — | $CH_3CN$ | 4.0 | 25 | 16 | acetamide 0.35 g | 60 |
| 37 | 4-Me-phenyl | potassium ion | $Ph(PhCN)_2Cl_2$ 40 mg | PhCN 2 cm³ | — | $ClCH_2$ $CH_2Cl$ 10 cm³ | 5.0 | 25 | 16 | ethyl-cyclohexyl-amine 0.65 g | 55 |
| 38 | 2-Cl-phenyl | potassium ion | $Pd(PhCN)_2Cl_2$ 60 mg | — | $Et_3(PhCH_2)$ $N^+Cl^-$ 50 mg | $CH_3CN$ | 4.2 | 25 | 16 | dicyclohexyl-amine 1.0 g | 50 |
| 39 | 2-Br-phenyl | potassium ion | $Pt(Ph_3P)_4$ 10 mg $Pd(PhCN)_2Cl_2$ 50 mg | — | — | $CH_3CN$ | 4.0 | 25 | 16 | acetamide 0.4 g | 60 |
| 40 | phenyl | potassium ion | $PdCl_2$ 35 mg | PhCN 1 cm³ | — | $CH_2Cl_2$ | 4.0 | 60 | 5 | benzol-sulphon-amide 0.9 g | 78 |

EXAMPLE 41

1.22 g (5 mmole) of potassium N-chloro-p-toluenesulphonamidate was carbonylated in 10 cm³ of acetonitrile minutes, while for amines of decreased basicity it is 8–16 hours. The amount of sulphonamidate is 10 mmole.

TABLE 5

Preparation of urea derivatives of the general formula (I)

| | Ar | M | catalyst | complex forming agent | additive | solvent | $P_{CO}$ [MPa] | Tempr. [°C.] | Time [hour] | (IV) reactant | Yield [%] |
|---|---|---|---|---|---|---|---|---|---|---|---|
| 42 | phenyl | potassium | $PdCl_2$ | $CH_3CN$ | — | $CH_2Cl_2$ | 4.0 | 25 | 5 | butyl-amine | 78 |

TABLE 5-continued

Preparation of urea derivatives of the general formula (I)

| | Ar | M | catalyst | complex forming agent | additive | solvent | $P_{CO}$ [MPa] | Tempr. [°C.] | Time [hour] | (IV) reactant | Yield [%] |
|---|---|---|---|---|---|---|---|---|---|---|---|
| 43 | phenyl | potassium ion | 62 mg Pd(PhCN)$_2$Cl$_2$ 100 g | 2 cm$^3$ PhCN 1 cm$^3$ | — | ClCH$_2$CH$_2$Cl | 3.2 | 60 | 2.2 | 0.8 g ethyl-butyl-amine | 82 |
| 44 | 4-Me-phenyl | sodium ion | Pd(Ph$_3$P)$_2$Cl$_2$ 110 mg | PhCN 1 cm$^3$ | (PhCH$_2$)Ph$_3$P$^+$Cl$^-$ 80 mg | CH$_2$Cl$_2$ | 5.0 | 40 | 2.5 | 1.1 g cyclohexyl-amine | 80 |
| 45 | 4-Me-phenyl | Bu$_4$N$^+$ | PdCl$_2$ 40 mg | — | — | CH$_3$CN | 4.2 | 25 | 1.5 | 1.1 g morpholine | 67 |
| 46 | 2-Cl-phenyl | potassium ion | Pd(PhCN)$_2$Cl$_2$ 100 mg | — | — | CH$_3$CN | 4.0 | 60 | 1.0 | 1.0 g urethane | 87 |
| 47 | 2-Br-phenyl | potassium ion | Pd(Ph$_3$P)$_3$Cl 20 mg Pd(Ph$_3$P)$_2$Cl$_2$ 60 mg | — | — | CH$_3$CN | 3.7 | 60 | 1.5 | 2.0 g acetamide 2.0 g | 87 |
| 48 | phenyl | potassium ion | Pd(PhCN)$_2$Cl$_2$ 100 mg | PhCN 1 cm$^3$ | 18-crown-6 70 mg | CH$_2$Cl$_2$ | 7.0 | 25 | 2 | phenyl-car-bamate 1.5 g | 85 |
| 49 | 4-Me-phenyl | potassium ion | PdCl$_2$ 60mg | CH$_3$CN 0.5 cm$^3$ | — | CH$_2$Cl$_2$ | 4.0 | 100 | 0.5 | benzamide 2.0 g | 80 |
| 50 | 2-naphthyl | potassium ion | Pd(PhCN)$_2$Cl$_2$ 100 mg | — | — | CH$_3$CN | 4.0 | 25 | 3.0 | butyl-amine | 80 85 |
| 51 | 4-Me-phenyl | sodium ion | PdCl$_2$ 100 mg | CH$_3$CN 0.2 cm$^3$ | — | CH$_2$Cl$_2$ | 5.0 | 20 | 4 | diallyl-amine 0.97 g | 72 |
| 52 | 4-Me-phenyl | sodium ion | PdCl$_2$ 21 mg | CH$_3$CN 0.2 cm$^3$ | — | CH$_2$Cl$_2$ | 5.0 | 20 | 8 | hexa-methylene amine 0.99 g | 78 |

We claim:

1. A process for preparing an arylsulfonyl isocyanate of formula I

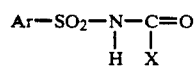

$$Ar-SO_2-N-C=O \quad (I)$$
$$\phantom{Ar-SO_2-N-}|\phantom{-}|$$
$$\phantom{Ar-SO_2-N-}H\phantom{-}X$$

and addition derivatives thereof, wherein Ar is an unsubstituted or a C$_{1-4}$ alkyl substituted phenyl, and H and X together are a chemical bond, which comprises (a) carbonylating an N-haloarylsulfonamide of formula II

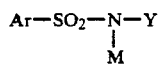

$$Ar-SO_2-N-Y \quad (II)$$
$$\phantom{Ar-SO_2-N-}|$$
$$\phantom{Ar-SO_2-N-}M$$

wherein

Ar is as defined above, Y is a chlorine or bromine atom, M is a sodium, potassium, quaternary ammonium, or a quaternary phosphonium ion, in the presence of a carbonylating catalyst, carbon monoxide, and from 0% to a catalytically effective amount of a phase transfer catalyst.

2. The process of claim 1, wherein said carbonylating catalyst is a palladium complex that was prepared previously or is prepared in situ, in which the coordination bond is formed by one or more of carbon, nitrogen, oxygen, phosphorus, sulfur, and halogen atoms, in the form of a homogenous, heterogenous, or immobilized homogenous catalyst, or the palladium complex is used together with from 10$^{-2}$ to 10% by weight based on the starting N-halosulfonamidate of a carbonyl of an element of group VI of the periodic table, or of a metal or metal complex of a metal of group VIII of the periodic table, in the presence of 0% or from 10$^{-1}$ to 10% by weight same basis of a phase transfer catalyst, wherein the reaction is carried out over 0.5 to 24 hours in a solvent at a temperature between 0.5° and 130° C., under carbon monoxide of a starting pressure of from 0.3 to 10 MPa, and then recovering the product.

3. The process of claim 1, wherein Y in formula II is chlorine, M is a potassium or quaternary ammonium ion.

4. The process of claim 1, wherein said carbonylating is carried out in the presence of a quaternary ammonium salt, quaternary phosphonium salt, or a crown ether transfer catalyst.

5. The process of claim 1, wherein carbonylating is carried out at a temperature between 25° C. and 100° C.

6. The process of claim 1, wherein a C$_{1-2}$ halogenated hydrocarbon, acetonitrile, or benzonitrile is used as a solvent.

7. The process of claim 1, wherein in formula I Ar is phenyl, or 4-Me-phenyl.

8. The process of claim 2, wherein a palladium catalyst is employed, together with at least one of a carbonyl of a metal from group VI of the periodic table, and a complex of a metal from group VIII of the periodic table.

* * * * *